(12) United States Patent
Sharma et al.

(10) Patent No.: US 9,556,138 B2
(45) Date of Patent: Jan. 31, 2017

(54) METHOD OF TREATMENT FOR ACNE AND AN ANTI-ACNE FORMULATION

(71) Applicant: PIRAMAL ENTERPRISES LIMITED, Mumbai, Maharashtra (IN)

(72) Inventors: Somesh Sharma, Maharashtra (IN);
Ashish Suthar, Maharashtra (IN);
Kavita Salkar, Maharashtra (IN);
Sandip Kedar, Maharashtra (IN)

(73) Assignee: PIRAMAL ENTERPRISES LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/384,599

(22) PCT Filed: Mar. 12, 2013

(86) PCT No.: PCT/IN2013/000150
§ 371 (c)(1),
(2) Date: Sep. 11, 2014

(87) PCT Pub. No.: WO2013/164841
PCT Pub. Date: Nov. 7, 2013

(65) Prior Publication Data
US 2015/0011619 A1    Jan. 8, 2015

(30) Foreign Application Priority Data
Mar. 12, 2012  (IN) .............. 647/MUM/2012

(51) Int. Cl.
| | |
|---|---|
| *C07D 311/16* | (2006.01) |
| *A61K 8/97* | (2006.01) |
| *A61K 31/37* | (2006.01) |
| *A61K 9/00* | (2006.01) |
| *A61Q 19/00* | (2006.01) |
| *A61K 8/49* | (2006.01) |
| *A61K 36/73* | (2006.01) |

(52) U.S. Cl.
CPC ............ *C07D 311/16* (2013.01); *A61K 8/498* (2013.01); *A61K 8/97* (2013.01); *A61K 9/0014* (2013.01); *A61K 31/37* (2013.01); *A61K 36/73* (2013.01); *A61Q 19/008* (2013.01)

(58) Field of Classification Search
CPC ......... C07D 311/16; A61K 36/73; A61K 8/97; A61Q 19/008; A61Q 8/498; A61Q 9/0014; A61Q 31/37
See application file for complete search history.

(56) References Cited

U.S. PATENT DOCUMENTS

2010/0273877 A1*  10/2010  Aoki et al. .................. 514/547

FOREIGN PATENT DOCUMENTS

| | | |
|---|---|---|
| WO | 98/17293 A1 | 4/1998 |
| WO | 98/25608 A1 | 6/1998 |
| WO | 2005/105124 A1 | 11/2005 |

OTHER PUBLICATIONS

Verotta, L.,"4-Alkyl-and 4-phenylcoumarins from Mesua ferrea as promising multidrug resistant antibacterials." Phytochemistry 65.21 (2004): 2867-2879.*
McKim, A. S., "Dimethyl sulfoxide USP, PhEur in approved pharmaceutical products and medical devices." (2008) p. 1-6.*

(Continued)

*Primary Examiner* — Samantha Shterengarts
*Assistant Examiner* — Matt Mauro
(74) *Attorney, Agent, or Firm* — Ladas & Parry LLP

(57) ABSTRACT

The present disclosure relates to an anti-acne formulation comprising at least one active ingredient selected from the group consisting of coumarin based compounds of Formula I and Formula II;

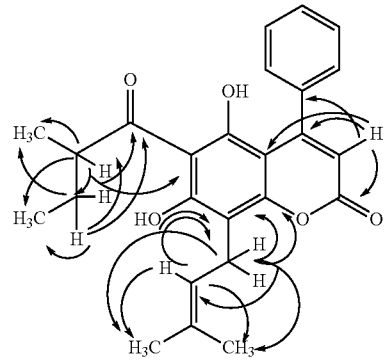

Formula I

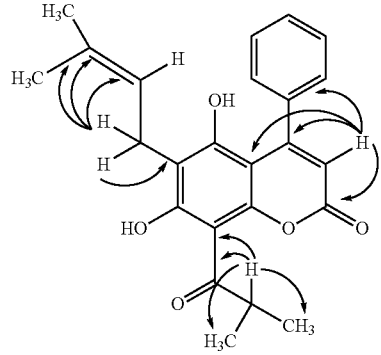

Formula II or pharmaceutically acceptable salts, polymorphs and derivatives thereof, and at least one pharmaceutically acceptable excipient. The present disclosure also relates to its application for preventing/curing/treating various acne conditions.

14 Claims, No Drawings

(56) References Cited

OTHER PUBLICATIONS

Brüggemann, H.,"The complete genome sequence of Propionibacterium acnes, a commensal of human skin." Science 305.5684 (2004): 671-673.*
International Search Report dated Jan. 22, 2014 for Application No. PCT/IN2013/000150.
Marquez, et al., "Mesuol, a natural occurring 4-phenylcoumarin, inhibits HIV-1 replication by targeting the NF-$_K$B pathway", Antiviral Research 66(2-3), 2005, abstract.

* cited by examiner

METHOD OF TREATMENT FOR ACNE AND AN ANTI-ACNE FORMULATION

RELATED APPLICATION INFORMATION

This application is a 371 of International Patent Application No. PCT/IN2013/000150 filed 12 Mar. 2013, which claims priority to India Patent Application No. 647/MUM/2012 filed 12 Mar. 2012, the contents of which are incorporated herein by reference.

FIELD OF THE DISCLOSURE

The present disclosure relates an anti-acne formulation. The present disclosure also relates to a method of treatment for acne.

BACKGROUND

Acne is a common human skin disease, which is characterized by areas of skin with seborrhea (scaly red skin), comedones (blackheads and whiteheads), papules (pinheads), pustules (pimples), nodules (large papules) and possibly scarring. Acne affects mostly skin with the densest population of sebaceous follicles. These areas include face, upper part of chest and the back. Severe acne is inflammatory, but acne can also manifest in non-inflammatory forms.

Acne occurs most commonly during adolescence and affects more than 96% of teenagers which often continues into adulthood. In adolescence, acne is usually caused by an increase in male sex hormones, which people of both genders accrue during puberty.

Acne scars are the result of inflammation within the dermis brought on by acne. The scar is created by the wound trying to heal itself resulting in too much collagen in one spot. Physical acne scars are often referred to as "Icepick" scars. This is because the scars tend to cause an indentation in the skin's surface.

Pigmented scars are usually the result of nodular or cystic acne (the painful 'bumps' lying under the skin). They often leave behind an inflamed red mark. Often, the pigmentation scars can be avoided simply by avoiding aggravation of the nodule or cyst. When sufferers try to 'pop' cysts or nodules, pigmentation scarring becomes significantly worse and may even bruise the affected area. Pigmentation scars nearly always fade with time taking between three months to two years to do so, however it can also persist.

Causes of Acne:

Acne develops as a result of blockages in follicles. Hyperkeratinization and formation of a plug of keratin and sebum (a microcomedo) is the earliest change. Enlargement of sebaceous glands and an increase in sebum production occur with increased androgen (DHEA-S) production at adrenarche. The microcomedo may enlarge to form an open comedone (blackhead) or closed comedone (milia). Comedones are the direct result of sebaceous glands' becoming clogged with sebum, a naturally occurring oil and dead skin cells. In these conditions, the naturally occurring largely commensal bacterium Propionibacterium acnes can cause inflammation, leading to inflammatory lesions (papules, infected pustules, or nodules) in the dermis around the microcomedo or comedone which results in redness and may result in scarring or hyperpigmentation.

Hormonal

Hormonal activity, such as menstrual cycles and puberty, may contribute to, the formation of acne. During puberty, an increase in male sex hormones called androgens causes the follicular glands to grow larger and make more sebum. Use of anabolic steroids may have a similar effect. Several hormones have been linked to acne: the androgens testosterone, dihydrotestosterone (DHT) and dehydroepiandrosterone sulfate (DHEAS), as well as insulin-like growth factor 1 (IGF-I).

Development of acne vulgaris in later years is uncommon, although this is the age group for rosacea, which may have similar appearances. True acne vulgaris in adult women may be a feature of an underlying condition such as pregnancy and disorders such as polycystic ovary syndrome or the rare Cushing's syndrome. Menopause-associated acne occurs as production of the natural anti-acne ovarian hormone estradiol fails at menopause. The lack of estradiol also causes thinning hair, hot flashes, thin skin, wrinkles, vaginal dryness, and predisposes to osteopenia and osteoporosis as well as triggering acne.

Genetic

The tendency to develop acne runs in families. For example, school aged boys with acne often have other members in their family with acne, as well. A family history of acne is associated with an earlier occurrence of acne and an increased number of retentional acne lesions.

Psychological

While the connection between acne and stress has been debated, scientific research indicates that "increased acne severity" is "significantly associated with increased stress levels. The National Institutes of Health (USA) list stress as a factor that "can cause an acne flare.

Infectious

*Propionibacterium acnes* (*P. acnes*) is the anaerobic bacterium which may be involved in formation of acne.

Diet

A high glycemic load diet and cow's milk have been associated with worsening acne.

EXISTING KNOWLEDGE

Different treatments exist for acne including benzoyl peroxide, antibiotics, retinoids, antiseborrheic medications and nicotinamide. Apart from these treatments, keratolytic soaps such as soap containing 3% Salicylic acid and 10% Sulfur are used as adjuvant agents in the treatment of acne which help to reduce the oiliness of skin. The available drugs are believed to work in at least 4 different ways including: normalising shedding into the pore to prevent blockage, killing *Propionibacterium acnes*, anti-inflammatory effects and hormonal manipulation.

However, the available treatments take longer time to treat the acne. Apart from this, the treatments do not provide a complete cure of acne and leaves mark or scar on the skin.

Therefore, there is envisages an anti-acne formulation containing plant derived phyto-constituents which can provide effective treatment for acne.

OBJECTS

Some of the objects of the present disclosure aimed to ameliorate one or more problems of the prior art or to at least provide a useful alternative are described herein below:

It is an object of the disclosure to provide a formulation comprising at least one plant derived active substance that is, useful for treatment of acne, post acne scar and post acne hyper pigmentation scars.

It is another object of the disclosure to provide a formulation comprising at least one plant derived active substance, which completely eliminate or attenuate the skin scars.

It is still another object of the disclosure to provide a formulation comprising at least one plant derived active substance, which shows high inhibitory activity against *Propionibacterium acnes*.

It is yet another object of the disclosure to provide a method of treatment of acne using plant derived active substances.

It is further object of the disclosure to provide a formulation which is non-greasy and which does not form a dull or sticky liquid film on the skin.

It is still further object of the disclosure to provide a thermally stable formulation.

SUMMARY

In accordance with one aspect of the present disclosure there is provided an anti-acne formulation comprising;

at least one active ingredient selected from the group consisting of coumarin based compounds of Formula I and Formula II;

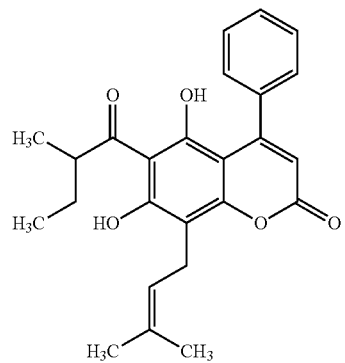

Formula I

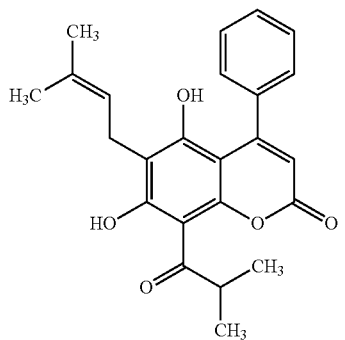

Formula II or pharmaceutically acceptable salts, polymorphs and derivatives thereof, and at least one pharmaceutically acceptable excipient, wherein the amount of said phyto-constituents ranges between 0.001 and 25% with respect to the total mass of the formulation.

Typically, the compounds of formula I or Formula II are derived from at least one plant material selected form the group consisting of *Mammea longifolia, Mammea americana, Mammea africana*, and *Mesua ferrea*.

Typically, said formulation is in the form of powder, cream, ointment, lotion, gel, cake, stick, soap and shampoo.

Typically, the excipient is at least one selected from the group consisting of surfactants, oils, waxes, thickening agents (gelling agent), emollients, preservatives, vehicle, perfume and colorants.

Typically, the excipient includes surfactant selected from the group consisting of alkyl polyethylene oxide, alkylphenol polyethylene oxide, sodium laureth sulphate, sodium dodecyl sulphate, alkyl alcohol, sodium lauryl sulfate, polyoxyethylene/polyoxypropylene block polymers (poloxamers), glycerols, polyglycerols, fatty acids, polyethylene glycol hydroxy stearate, Cetomacrogol-1000, cetostearyl alcohol, polyalkyl glucosides, ceramides, polyethylene glycol/alkyl glycol copolymers, and polyethylene glycol/polyalkylene glycol ether di-block or tri-block copolymers, phenoxy ethanol diacetylated monoglycerides, diethylene glycol monostearate, ethylene glycol monostearate, glyceryl monooleate, propylene glycol monostearate, macrogol esters, macrogol stearate, polyoxyethylene 50 stearate, macrogol ethers, cetomacrogel 1000, lauromacrogols, nonoxynols, octoxinols, tyloxapol, polyvinyl alcohols, polysorbate, sorbitan monolaurate, sorbitan monooleate, sorbitan monopalmitate, sorbitan sesquioleate, sorbitan trioleate, sorbitan tristearate, sucrose esters, cetyl alcohol, oleyl alcohol, cetylpyridinium chloride, cetyl trimethylammonium bromide, Tween® 20 and Tween® 80.

Typically, the excipient includes oil selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, butylene glycol dicaprylate/dicaprate, caprylic/capric triglyceride, olive oil, sunflower oil, soybean oil, peanut oil, grapeseed oil, almond oil, palm oil, coconut oil, palm kernel oil, castor oil, wheat germ oil, grape seed oil, thistle oil, silicon oils, lanolin oil, avocado oil and macadamia oil.

Typically, the excipient includes wax selected from the group of candelilla wax, carnauba wax, bees wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin wax, sunflower wax, lemon wax, grape fruit wax and laurel wax.

Typically, the excipient includes thickening agent selected from the group consisting of hydroxypropyl methylcellulose, hydroxypropyl cellulose, sodium carboxy methyl cellulose, hydroxyethyl cellulose, carbopol polyethylene glycol, acrylates, methacrylates, gelatin, alginates, pectins, tragacanth, karaya gum, xanthan gum, carrageenin, agar, alginate, chitosan and acacia.

Typically, the excipient includes emollient selected from the group consisting of stearic acid, caprylic acid, oleic acid, palmitic acid, lauric acid, cetyl alcohol, lauryl alcohol, stearyl alcohol, cetearyl alcohol, oleyl alcohol, octyl palmitate, octyl stearate, glyceryl stearate, propylene glycol, dicaprate, dicaprylate and cetyl palmitate.

Typically, the excipient includes preservative selected from the group consisting of benzalkonium chloride, benzyl alcohol, methyl paraben, propyl paraben, butyl paraben, chlorobutanol, metacresol, phenylmercuric nitrate, thiomersal, myristyl gamma picolinium chloride, sorbic acid, potassium sorbate and phenol. The formulation is typically used for preventing/curing/treating at least one acne condition, selected from the group consisting of inflamed patches, post acne scar and post acne hyperpigmentation scar.

In accordance with another aspect of the present disclosure there is provided a method for preventing/curing/treating at least one acne condition, said method comprising applying a therapeutically effective amount of formulation as claimed in claim 1 to a subject.

Typically, the formulation may be applied to said subject in single or plurality of doses or daily.

DETAILED DESCRIPTION

In an effort to develop a novel anti-acne formulation for treating or preventing acnes, the inventors of the present disclosure performed extensive experiments using coumarin based compounds/phyto-constituents of Formula I and Formula II against *Propionibacterium acnes*. It was surprisingly found that these phyto-constituents/compounds of the present disclosure shows enhanced anti-acne activity. Particularly, it was found that the compounds of the present disclosure are effective against acne condition at a very low concentration i.e. these compound/s is effective in an amount of 50 ng to 500 ng/ml.

Further in view of the preliminary findings, the inventors developed an anti-acne formulation, which comprises coumarin based compounds/phyto-constituents of Formula I and/or Formula II or pharmaceutically acceptable salts, polymorphs and derivatives thereof, Formula I

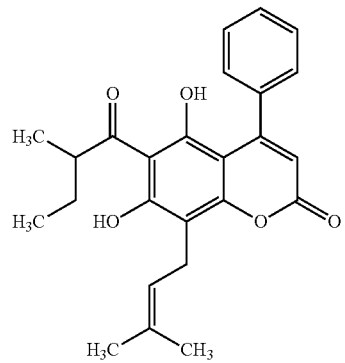

Formula II

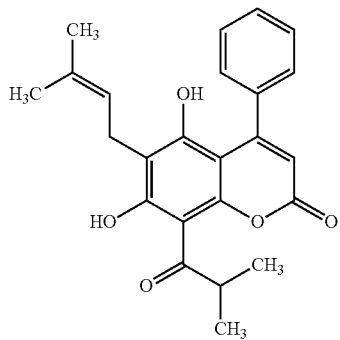

along with at least one pharmaceutically acceptable excipient.

Typically, the amount of the coumarin based compounds/phyto-constituents of Formula I and/or Formula II is maintained in the range of 0.001 to 25% with respect to the total mass of the formulation.

In accordance with one embodiment of the present disclosure the compound/s of Formula I or Formula II is derived from at least one plant material selected form the group consisting of *Mammea longifolia*, *Mammea americana*, *Mammea africana*, and *Mesua ferrea*.

In accordance with another embodiment of the present disclosure the compound/s of Formula I or Formula II is derived synthetically or semi-synthetically using synthesis processes of the prior art.

*Mammea longifolia*.

Description: It is a big tree with very pretty and glossy foliage. Leaves-thickly coriaceous, 16-20 cm. by 5-6.5 cm, oblong, obtuse, glabrous, petioles 6 mm. long. Fruit—2.5 cm long, obliquely ovoid, single seed. Flowers-numerous, in short fascicles on tubercles from the axils of fallen leaves, orange red colored; stamens many, sterile & short in female flowers. The dried flower buds are light brown in color and round in shape. Tiny flowers are borne in clusters on the tree trunk and mature branches.

Family: Clusiaceae

Synonym: *Ochrocarpus longifolius*

Chemical constituents: The flower buds of *Mammea longifolia* have been reported to contain 0.50-1.5% volatile oil and 5-6% oleoresins. Sesquiterpenes are the predominant constituents of the oil, while major compounds are b-caryophyllene (28.25%), d-cadinene (14.22%), a-copaene (5.24%), linalool (3.46%), a-humulene (4.63%), and a-muurolene (3.35%). Phytochemical screening of the methanolic extract of the crude drug (flower buds) identified presence of glycosides, reducing sugars, phenolics, tannins, four alkylated coumarins—Surangin A and B, Squalene, Cycloartenol; campesterol, stigmasterol and bsitosterol, flavanoids, saponins and volatile oil.

Uses: *Mammea longifolia* exhibits antibacterial activity against both Gram-positive and Gram-negative organisms. Vitexin and Meso-inositol isolated from this plant exhibited positive effect on treatment of leprosy. Surangin B, a coumarin isolated from *Mammea longifolia* was shown to have antifungal and antihelminthic activity

*Mammea americana*.

Description: The mammee tree is 18-21 m high and reaches 1.9-1.2 m in diameter. The tree's upright branches form an oval head. Its dark-green foliage is quite dense, with opposite, leathery, elliptic leaves. The flowers are borne either singly or in clusters of two or three; on short stalks. There can be, in a single flower, pistils, stamens or both, so there can be male, female or hermaphrodite flowers on one tree.

Family: Clusiaceae

Synonym: mamey, mammee apple, mamme, mammy-apple, South American apricot, tropical apricot, *Mammea emarginata*.

Geographical source and distribution: Native to the West Indies and northern South America.

Chemical constituents: phenyl coumarins, xanthones, triterpenoids, fats and flavonoids.

Uses: *Mammea* coumarins express a wide range of bio-activities, such as insecticidal, antioxidant, anticancer, anti-HIV, antifungal, antibacterial, antimicrobial, and antibiotic activities

*Mammea africana*.

Description: It is a large forest tree of 50-100 feet high with bark often yellow with pale scales and resinous yellow sap.

Family: Clusiaceae

Synonym: *Ochrocarpus africana*

Geographical source and distribution: The plant is widely distributed in tropical Africa.

Chemical constituents: 5,-7-dihydroxy-8-(12-methyl-butryl)-4-N-Pentyl coumarins, Mesuxanthone B.

Uses: It is used traditionally in the treatment of malaria, diabetes, internal heat, stomach pains, rheumatism pains, scabies, cough, hypertension and microbial infections. It also has antimicrobial activity against *Staphylococcus aureus*.

*Mesua ferrea.*

Description: It is a medium to large sized tree that can attain a height between 18 and 30 m, with reddish-brown to grey colored bark that peels off in thin flakes, the wood is extremely hard.

Family: Clusiaceae

Synonym: Nagassor, *Mesua nagassarium*

Geographical source and distribution: It is widely distributed in tropical countries like India, Burma, Thailand, Indochina and New Guinea.

Chemical constituents: linoleic, oleic, stearic, and arachidic acids, mesuol, mesuagin, mammeisin, mammeigin, mesuone 4-alkylcoumarins ferruols A and B, a lupeol-type triterpenoid guttiferol, mesuaxanthones A and B, ferraxanthone 1,7-dihydroxyxanthone,1,5-dihydroxy-3-methoxyxanthone,1X6-trihydroxyxanthone, 1,5-dihydroxyxanthone, I-hydroxy-7-methoxyxanthone and β-sitosterol. Stamens give α and β-amyrin, β-sitosterol, biflavonoids-mesuaferrones A and B, mesuanic acid, 1,5-dihydroxyxanthone, euxanthone 7-methyl ether and β-sitosterol Uses: it is used as antiseptic, purgative, blood purifier, worm control, tonic properties carminative, expectorant, cardiotonic, diuretic and antipyretic agent.

Typically, the formulation is in the form selected from the group consisting of powder, cream, ointment, lotion, gel, cake, stick, soap and shampoo.

Typically, the pharmaceutically acceptable excipient is at least one selected from the group consisting of surfactants, oils, waxes, thickening agents (gelling agent), emollients, preservatives, vehicle, perfume and colorants.

Typically, the surfactant is selected from the group of alkyl polyethylene oxide, alkylphenol polyethylene oxide, sodium laureth sulphate, sodium dodecyl sulphate, alkyl alcohol, cetostearyl alcohol, sodium lauryl sulfate, polyoxyethylene/polyoxypropylene block polymers (poloxamers), glycerols, polyglycerols, fatty acids, polyethylene glycol hydroxy stearate, polyalkyl glucosides, ceramides, polyethylene glycol/alkyl glycol copolymers, and polyethylene glycol/polyalkylene glycol ether di-block or tri-block copolymers, Phenoxy ethanol diacetylated monoglycerides, diethylene glycol monostearate, ethylene glycol monostearate, glyceryl monooleate, propylene glycol monostearate, macrogol esters, macrogol stearate, polyoxyethylene 50 stearate, macrogol ethers, lauromacrogols, nonoxynols, octoxinols, tyloxapol, polyvinyl alcohols, polysorbate, sorbitan monolaurate, sorbitan monooleate, sorbitan monopalmitate, sorbitan sesquioleate, sorbitan trioleate, sorbitan tristearate, sucrose esters, cetyl alcohol, oleyl alcohol, cetylpyridinium chloride, cetyl trimethylammonium bromide, Tween® 20, Tween® 80 and combinations thereof.

Typically, the oil is at least one selected from the group consisting of isopropyl myristate, myristyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, ethylhexyl cocoate, dicaprylyl carbonate, cetearyl isononanoate, oleyl erucate, erucyl oleate, erucyl erucate, octyldodecanol, polydecenes, squalane, dicaprylyl ether, butylene glycol dicaprylate/dicaprate, caprylic/capric triglyceride, olive oil, sunflower oil, soybean oil, peanut oil, grapeseed oil, almond oil, palm oil, coconut oil, palm kernel oil, castor oil, wheat germ oil, grape seed oil, thistle oil, silicon oils, lanolin oil, avocado oil and macadamia oil.

Typically, wax is at least one selected from the group of candelilla wax, carnauba wax, bees wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin waxes, sunflower wax, lemon wax, grape fruit wax and laurel wax.

Typically, the thickening agent includes hydroxypropyl methylcellulose, hydroxypropyl cellulose, sodium carboxy methyl cellulose, hydroxyethyl cellulose, carbopol polyethylene glycol, acrylates, methacrylates, gelatin, alginates, pectins, tragacanth, karaya gum, xanthan gum, carrageenin, agar, alginate, chitosan and acacia.

Typically, emollient is at least one selected from the group consisting of stearic acid, caprylic acid, oleic acid, palmitic acid, lauric acid, cetyl alcohol, lauryl alcohol, stearyl alcohol, cetearyl alcohol, oleyl alcohol, octyl palmitate, octyl stearate, glyceryl stearate, propylene glycol, dicaprate, dicaprylate and cetyl palmitate.

Typically, preservative is at least one selected from the group consisting of benzalkonium chloride, benzyl alcohol, methyl paraben, propyl paraben, butyl paraben, chlorobutanol, metacresol, phenylmercuric nitrate, thiomersal, myristyl gamma picolinium chloride, sorbic acid, potassium sorbate and phenol.

Typically, perfume is at least one selected from the group consisting of citrus musk, floral woody, citrus musk woody, fresh bouquet, musk, floral musk, lavender oil, jasmine oil, rose oil, cedarwood oil, sandalwood oil, orange oil and lemon oil.

The disclosure will now be described with the help of the following non-limiting examples.

EXAMPLE 1

A formulation in the form of a cream, was prepared using the following ingredients:

TABLE 1

| Sr. No. | Ingredient | Quantity (% w/w) |
| --- | --- | --- |
| 1 | Mammea A/AB (Formula I) | 5 |
| 2 | Cetostearyl alcohol | 11.56 |
| 3 | Cetomacrogol - 1000 | 3.21 |
| 4 | Sorbitan mono-oleate | 1.60 |
| 5 | Glycerol monostearate | 2.25 |
| 6 | Isopropyl myristate | 1.92 |
| 7 | Stearic acid | 1.92 |
| 8 | Sodium methyl paraben | 0.20 |
| 9 | Sodium propyl paraben | 0.02 |
| 10 | Phenoxy ethanol | 0.50 |
| 11 | Sodium EDTA | 0.02 |
| 12 | Carbopol - 940 | 0.20 |
| 13 | Sodium lauryl sulphate | 0.75 |
| 14 | Simethicone | 1.00 |
| 15 | Propylene glycol | 7.74 |
| 16 | Demineralized water | q.s. |

Procedure

In the first step, 5 gm of *Mammea* A/AB (Formula I) was mixed in 3 ml of Propylene glycol to obtain suspension of *Mammea* A/AB.

In the second step, 11.56 ml of Cetostearyl alcohol, 3.21 gm of Cetomacrogol-1000, 1.60 gm of Sorbitan monooleate, 2.25 ml of Glycerol monostearate and 1.92 gm of Isopropyl myristate were melted separately.

In the third step, 0.20 gm of Sodium methyl paraben and Sodium propyl paraben along with 0.75 gm of Sodium lauryl sulphate were mixed with demineralized water.

In the fourth step, 0.20 gm Carbopol-940 was mixed with demineralized water and the mixture was kept for swelling. To this 0.02 gm of Sodium EDTA and 1 gm of Simethicon were added.

The contents of all steps along with remaining quantity of Propylene glycol and demineralized water were mixed at a temperature of 55° C., homogenized, and allowed to cool to obtain an anti-acne cream of the present disclosure.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

"Whenever a range of values is specified, a value up to 10% below and above the lowest and highest numerical value respectively, of the specified range, is included in the scope of the invention".

While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. An anti-acne formulation consisting of;
at least one active ingredient selected from the group consisting of coumarin based compounds of Formula I and Formula II;

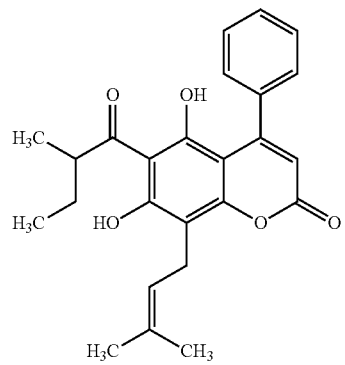

Formula I

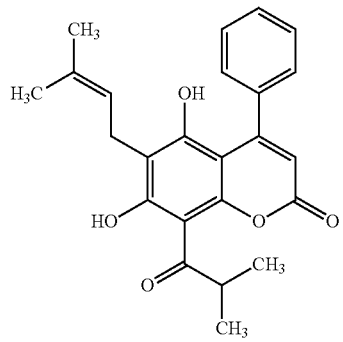

Formula II or pharmaceutically acceptable salts and polymorphs thereof, and
at least one pharmaceutically acceptable excipient, wherein the amount of said active ingredient(s) ranges between 0.001 and 25% with respect to the total mass of the formulation.

2. The formulation as claimed in claim 1, wherein the compounds of formula I or formula II are derived from at least one plant material selected from the group consisting of *Mammealongifolia, Mammeaamericana, Mammeaafricana*, and *Mesuaferrea*.

3. The formulation as claimed in claim 1, wherein said formulation is in the form selected from the group consisting of powder, cream, ointment, lotion, gel, cake, stick, soap and shampoo.

4. The formulation as claimed in claim 1, wherein the excipient is selected from at least one of the group consisting of surfactants, oils, waxes, thickening agents, emollients, preservatives, vehicle, perfume and colorants.

5. The formulation as claimed in claim 4, wherein the excipient includes surfactant selected from the group consisting of alkyl polyethylene oxide, alkylphenol polyethylene oxide, sodium laureth sulphate, sodium dodecyl sulphate, alkyl alcohol, sodium lauryl sulfate, polyoxyethylene/polyoxypropylene block polymers (poloxamers), glycerols, polyglycerols, fatty acids, polyethylene glycol hydroxy stearate, Cetomacrogol-1000, cetostearyl alcohol, polyalkyl glucosides, ceramides, polyethylene glycol/alkyl glycol copolymers, and polyethylene glycol/polyalkylene glycol ether di-block or tri-block copolymers, phenoxy ethanol diacetylated monoglycerides, diethylene glycol monostearate, ethylene glycol monostearate, glyceryl monooleate, propylene glycol monostearate, macrogol esters, macrogol stearate, polyoxyethylene 50 stearate, macrogol ethers, lauromacrogols, nonoxynols, octoxinols, tyloxapol, polyvinyl alcohols, polysorbate, sorbitanmonolaurate, sorbitanmonooleate, sorbitanmonopalmitate, sorbitansesquioleate, sorbitantrioleate, sorbitantristearate, sucrose esters, cetyl alcohol, oleyl alcohol, cetylpyridinium chloride, cetyltrimethylammonium bromide, Tween 20 and Tween 80.

6. The formulation as claimed in claim 4, wherein the excipient includes oil selected from the group consisting of isopropyl myristate, myristylmyristate, isopropyl palmitate, isopropyl stearate, isopropyl oleate, n-butyl stearate, n-hexyl laurate, n-decyloleate, isooctyl stearate, isononyl stearate, isononylisononanoate, 2-ethylhexyl palmitate, 2-ethylhexyl laurate, 2-hexyldecyl stearate, 2-octyldodecyl palmitate, oleyloleate, ethylhexylcocoate, dicaprylyl carbonate, cetearylisononanoate, oleylerucate, erucyloleate, erucylerucate, octyldodecanol, polydecenes, squalane, dicaprylyl ether, butylene glycol dicaprylate/dicaprate, caprylic/capric-triglyceride, olive oil, sunflower oil, soybean oil, peanut oil, grape seed oil, almond oil, palm oil, coconut oil, palm kernel oil, castor oil, wheat germ oil, grape seed oil, thistle oil, silicon oils, lanolin oil, avocado oil and macadamia oil.

7. The formulation as claimed in claim 4, wherein the excipient includes wax selected from the group of candelilla wax, carnauba wax, bees wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresin, ozocerite (earth wax), paraffin wax, sunflower wax, lemon wax, grape fruit wax and laurel wax.

8. The formulation as claimed in claim 4, wherein the excipient includes thickening agent selected from the group consisting of hydroxypropyl methylcellulose, hydroxypropyl cellulose, sodium carboxy methyl cellulose, hydroxyethyl cellulose, carbopol polyethylene glycol, acrylates, methacrylates, gelatin, alginates, pectins, tragacanth, karaya gum, xanthan gum, carrageenin, agar, alginate, chitosan and acacia.

9. The formulation as claimed in claim 4, wherein the excipient includes emollient selected from the group consisting of stearic acid, caprylic acid, oleic acid, palmitic acid, lauric acid, cetyl alcohol, lauryl alcohol, stearyl alcohol, cetearyl alcohol, oleyl alcohol, octylpalmitate, octyl stearate, glyceryl stearate, propylene glycol, dicaprate, dicaprylate and cetylpalmitate.

10. The formulation as claimed in claim 4, wherein the excipient includes preservative selected from the group consisting of benzalkonium chloride, benzyl alcohol, methyl paraben, propyl paraben, butyl paraben, chlorobutanol, metacresol, phenylmercuric nitrate, thiomersal, myristyl gamma picolinium chloride, sorbic acid, potassium sorbate and phenol.

11. The formulation as claimed in claim 4, wherein the excipient includes a perfume selected from the group consisting of, floral woody, fresh bouquet, musk, lavender oil, jasmine oil, rose oil, cedarwood oil, sandalwood oil, orange oil and lemon oil.

12. A method for treating at least one acne condition comprising applying a therapeutically effective amount of formulation as claimed in claim 1 to a subject in need thereof.

13. The method as claimed in claim 12, wherein the acne condition is selected from the group consisting of inflamed patches, post acne scar and post acne hyperpigmentation scar.

14. The method as claimed in claim 12, wherein the formulation may be applied to said subject in single or plurality of doses or daily.

\* \* \* \* \*